(12) United States Patent
Lal et al.

(10) Patent No.: US 6,358,711 B1
(45) Date of Patent: Mar. 19, 2002

(54) ANTIBODY TO HUMAN TESTIN AND METHODS OF MAKING AND USING

(75) Inventors: Preeti Lal, Santa Clara; Karl J. Guegler, Menlo Park; Neil C. Corley, Mountain View, all of CA (US)

(73) Assignee: Incyte Genomics, Inc., Palo Alto, CA (US)

( * ) Notice: Subject to any disclaimer, the term of this patent is extended or adjusted under 35 U.S.C. 154(b) by 0 days.

(21) Appl. No.: 09/571,347

(22) Filed: May 16, 2000

Related U.S. Application Data

(62) Division of application No. 09/369,675, filed on Aug. 5, 1999, which is a division of application No. 09/002,567, filed on Dec. 31, 1997, now Pat. No. 6,001,594.

(51) Int. Cl.[7] ........................ C12P 21/08; C07K 16/00
(52) U.S. Cl. ................ 435/70.21; 435/452; 530/387.1; 530/387.9; 530/388.1; 530/388.21; 424/185.1
(58) Field of Search ................ 530/387.1, 388.1; 424/185.1; 435/70.21, 452

(56) References Cited

U.S. PATENT DOCUMENTS 5,959,075 A * 9/1999 Lok et al. .................. 530/303

OTHER PUBLICATIONS

Way, J.C. and M. Chalfie, "mec–3, a Homeobox–Containing Gene That Specifies Differentiation of the Touch Receptor Neurons in C. elegans", *Cell*, 54: 5–16 (1988).

Freyd, G. et al., "Novel cysteine–rich motif and homeodomain in the product of the *Caenorhabditis elegans* cell lineage gene lin–II", *Nature*, 344: 876–879 (1990).

Higuchi, O. et al., "Inhibition of activated Ras–induced neuronal differentiation of PC12 cells by the LIM domain of LIM–kinase 1", *Oncogene*, 14: 1819–1825 (1997).

Sánchez–García, I. And T.H. Rabbitts, "The LIM domain: a new structural motif found in zinc–finger–like proteins", *Trends Genet.*, 10: 315–320 (1994).

Dawid, I. et al., "LIM domain proteins", *C.R. Acad. Sci.* 318: 295–306 (1995).

McGuire, E.A. et al., "Thymic Overexpression of Ttg–1 in Transgenic Mice Results in T–Cell Acute Lymphoblastic Leukemia/Lymphoma", *Mol. Cell. Biol.*, 12: 4186–4196 (1992).

Fisch, P. et al., "T–cell acute lymphoblastic lymphoma induced in transgenic mice by the *RBTN1* and *RBTN2* LIM–domain genes", *Oncogene*, 7: 2389–2397 (1992).

Divecha, N. and B. Charleston, "Cloning and characterisation of two new cDNAs encoding murine triple LIM domains", *Gene*, 156: 283–286 (1995).

Divecha, N. and B. Charleston, (Direct Submission), GenBank Sequence Database (Accession 475210), National Center for Biotechnology Information, National Library of Medicine, Bethesda, Maryland, 20894 (GI 475210) (1995).

Divecha, N. and B. Charleston, (Direct Submission), GenBank Sequence Database (Accession X78990), National Center for Biotechnology Information, National Library of Medicine, Bethesda, Maryland, 20894 (GI 475209; GI 475210) (1995).

Arber, S. et al., "Muscle LIM Protein, a Novel Essential Regulator of Myogenesis, Promotes Myogenic Differentiation", *Cell*, 79: 221–231 (1994).

Hillier, L. et al., (Direct Submission), GenBank Sequence Database (Accession AA026727), National Center for Biotechnology Information, National Library of Medicine, Bethesda, Maryland, 20894 (GI 1492508) (1997).

* cited by examiner

*Primary Examiner*—Christina Y. Chan
*Assistant Examiner*—Phuong Huynh
(74) *Attorney, Agent, or Firm*—Incyte Genomics, Inc.

(57) ABSTRACT

The invention provides a human testin (HTES) and polynucleotides which identify and encode HTES. The invention also provides expression vectors, host cells, antibodies, agonists, and antagonists. The invention also provides methods for treating or preventing disorders associated with expression of HTES.

2 Claims, 8 Drawing Sheets

```
                                          10              19              28              37              46              55
5' G  GAA  GTT  CGA  CGG  CGC  CGG  CGC  AGT  GGC  GCG  TGT  TGA  GCG  GCG  CCG  CGG  GAG  TTC  CGC 64              73              82              91             100             109
   AGG  TTT  CCC  GTG  TTC  GCA  GCG  GAG  GCA  GCT  GAA  CCC  GGC  CGT  GGG  ATC 118             127             136             145             154             163
   CCG  GAT  AGG  AGG  AGG  GGA  CCC  ATA  GGA  CGC  GTT  AAC  ATG  GAC  CTG  GAA  AAC
                                                                          M    D    L    E    N 172             181             190             199             208             217
   AAA  GTG  AAG  AAG  ATG  GGC  TTA  GGT  CAC  GAG  CAA  GGA  TTT  GGA  GCC  CCT  TGT  TTA
    K    V    K    K    M    G    L    G    H    E    Q    G    F    G    A    P    C    L 226             235             244             253             262             271
   AAA  TGC  AAA  GAA  AAA  TGT  GAA  GGA  TTC  CAC  TTC  TGG  AGA  AAA  ATA  TGT
    K    C    K    E    K    C    E    G    F    H    F    W    R    K    I    C 280             289             298             307             316             325
   CGT  AAC  TGC  AAG  TGT  GGC  CAA  GAA  GAG  CAT  GAT  GTC  CTC  TTG  AGC  AAT  GAA  GAG
    R    N    C    K    C    G    Q    E    E    H    D    V    L    L    S    N    E    E
```

FIGURE 1A

```
      334           343           352           361           370           379
GAT CGA AAA GTG GGA AAA CTT TTT GAA GAC ACC AAG TAT ACC ACT CTG ATT GCA
 D   R   K   V   G   K   L   F   E   D   T   K   Y   T   T   L   I   A 388           397           406           415           424           433
AAA CTA AAG TCA GAT GGA ATT CCC ATG TAT AAA CGC AAT GTT ATG ATA TTG ACG
 K   L   K   S   D   G   I   P   M   Y   K   R   N   V   M   I   L   T 442           451           460           469           478           487
AAT CCA GTT GCT GCC AAG AAT GTC TCC ATC AAT ACA GTT ACC TAT GAG TGG
 N   P   V   A   A   K   N   V   S   I   N   T   V   T   Y   E   W 496           505           514           523           532           541
GCT CCT GTC CAG AAT CAA GCA TTG GCC AGG CAG TAC ATG CAG ATG CTA CCC
 A   P   V   Q   N   Q   A   L   A   R   Q   Y   M   Q   M   L   P 550           559           568           577           586           595
AAG GAA AAG CAG CCA GTA GCA GGC TCA GAG GGG GCA CAG TAC CGG AAG AAG CAG
 K   E   K   Q   P   V   A   G   S   E   G   A   Q   Y   R   K   K   Q 604           613           622           631           640           649
CTG GCA AAG CAG CTC CCT GCA CAT GAC CAG GAC CCT TCA AAG TGC CAT GAG TTG
 L   A   K   Q   L   P   A   H   D   Q   D   P   S   K   C   H   E   L
```

FIGURE 1B

```
     658         667         676         685         694         703
TCT CCC AGA GAG GTG AAG GAG ATG GAG CAG TTT GTG AAG AAA TAT AAG AGC GAA
 S   P   R   E   V   K   E   M   E   Q   F   V   K   K   Y   K   S   E 712         721         730         739         748         757
GCT CTG GGA GTA GGA GAT GTC AAA CTT CCC TGT GAG ATG GAT GCC CAA GGC CCC
 A   L   G   V   G   D   V   K   L   P   C   E   M   D   A   Q   G   P 766         775         784         793         802         811
AAA CAA ATG AAC ATT CCT GGA GGG GAT AGA AGC ACC CCA GCA GTG GGG GCC
 K   Q   M   N   I   P   G   G   D   R   S   T   P   A   A   V   G   A 820         829         838         847         856         865
ATG GAG GAC AAA TCT GCT GAG CAC AAA AGA ACT CAA TAT TCC TGC TAT TGC
 M   E   D   K   S   A   E   H   K   R   T   Q   Y   S   C   Y   C   C 874         883         892         901         910         919
AAA CTG AGT ATG GAA GAA GGT GAC CCA GCC ATC TAT GCC GAA AGG GCT GGC TAT
 K   L   S   M   E   E   G   D   P   A   I   Y   A   E   R   A   G   Y 928         937         946         955         964         973
GAT AAA CTG TGG CAC CCA GCT TGT TTT GTC TGC TGC AGC ACC TGC CAT GAA CTC CTG
 D   K   L   W   H   P   A   C   F   V   C   C   S   T   C   H   E   L   L
```

FIGURE 1C

```
             982         991        1000       1009       1018       1027
GTT GAC ATG ATT TAT TTT TGG AAG AAT GAG AAG CTA TAC TGT GGC AGA CAT TAC
 V   D   M   I   Y   F   W   K   N   E   K   L   Y   C   G   R   H   Y
            1036        1045       1054       1063       1072       1081
TGT GAC AGC GAG AAA CCC CGA TGT GCT GGC TGT GAC GAG CTG ATA TTC AGC AAT
 C   D   S   E   K   P   R   C   A   G   C   D   E   L   I   F   S   N
            1090        1099       1108       1117       1126       1135
GAG TAT ACC CAG GCA GAA AAC CAG AAT TGG CAC CTG AAA CAC TTC TGC TGC TTT
 E   Y   T   Q   A   E   N   Q   N   W   H   L   K   H   F   C   C   F
            1144        1153       1162       1171       1180       1189
GAC TGT GAT AGC ATT CTA GCT GGG GAG ATA TAC GTG ATG GTC AAT GAC AAG CCC
 D   C   D   S   I   L   A   G   E   I   Y   V   M   V   N   D   K   P
            1198        1207       1216       1225       1234       1243
GTG TGC AAG CCC TGC TAT GTG AAG AAT CAC GCT GTG TGT CAA GGA TGC CAC
 V   C   K   P   C   Y   V   K   N   H   A   V   C   Q   G   C   H
            1252        1261       1270       1279       1288       1297
AAT GCC ATC GAC CCA GAA GTG CAG CGG GTG ACC TAT AAC AAT TTC AGC TGG CAT
 N   A   I   D   P   E   V   Q   R   V   T   Y   N   N   F   S   W   H
```

FIGURE 1D

```
              1306            1315            1324            1333            1342            1351
             GCA TCC ACA GAG TGC TTT CTG TGC TCT TGC TGC AGC AAA TGC CTC ATT GGG CAG
              A   S   T   E   C   F   L   C   S   C   C   S   K   C   L   I   G   Q 1360            1369            1378            1387            1396            1405
             AAG TTC ATG CCA GTA GAA GGG ATG GAA GTT TTC TGT TCA GTG GAA TGT AAG AAG AGG
              K   F   M   P   V   E   G   M   E   V   F   C   S   V   E   C   K   K   R 1414            1423            1432            1441            1450            1459
             ATG TCT TAG GAG GAG ACC CAG AAG TAT CGA GCC ATA GCT ATC CAA AGT GGT
              M   S 1468            1477            1486            1495            1504            1513
             CTG CAT TTC TAC TGT AAA ATG CAA TTT GAA AAA AAT AAA ACG CAA AAA AAG AAA 1522            1531            1540            1549            1558            1567
             CTG TAA AGG AAA CCA AGA GAT TTT GTT TAA TTT TTT TGG CCA TTT TTT CTT CAT 1576            1585            1594            1603            1612            1621
             CAA TTT TTT TTC GGT CTC AAC TTT TAA ACT TGG TTT AAG CAT TTG ATT TGT AAA 1630            1639            1648            1657            1666            1675
             ACA GTA AAT AAT TGT ATC TTT CCA TAG CTT TTC AAA TGT GAA ATC ATT TTT GGA
```

FIGURE 1E

```
     1684        1693        1702       1711       1720       1729
AGC TTG GAT CTC ATT AAA CTT CAT GTC TCT ATT CCA TTT GTG CCA CAC ACT TAA 1738        1747        1756       1765       1774       1783
AAG TTA GTG TAC TGA ATG GAA AGA TGA GCA TTC CTA GTT CTA CAC TTC TTT TTT 1792        1801        1810       1819       1828       1837
CCC CCT CAT GTG TAA AAT GAA AAG ACT AAA TTT GCC CTA ATA CCA AGG CGC 1846        1855        1864       1873       1882       1891
TAC GTT TAT TGC CTC GTC TTA TTC CAT GAC CTT TGT AAT GAT ACA CAG TGA ATT 1900        1909        1918       1927       1936       1945
CTT TTT GAC AAA GAG AAA TGC CGT GTA GTA TGC CGA GCT GCT GTT TTA ATG CCT 1954        1963        1972       1981       1990       1999
ATG CAT TTA CTC TTT TCT GAT TTA GGC AAA AGT GGC ATT TCC TTA ATG CAT TTC 2008        2017        2026       2035       2044       2053
TCA ATT TTT TAA AGG ACC CTA CTT CAG AAT CCC CTT TGA AGT TGT GAC TTG AAC 2062        2071        2080       2089
GGT GGC CTG AAA TTT TAT TAC CCC TGG GGC ATA ACA GAT CCC CC 3'
```

ANTIBODY TO HUMAN TESTIN AND METHODS OF MAKING AND USING

This application is a divisional application of U.S. application Ser. No. 09/369,675, filed on Aug. 5, 1999, pending, which is a divisional application of U.S. application Ser. No. 09/002,567, filed Dec. 31, 1997, issued Dec. 14, 1999, as U.S. Pat. No. 6,001,594, all of which applications and patents are hereby incorporated herein by reference.

FIELD OF THE INVENTION

This invention relates to nucleic acid and amino acid sequences of a human testin and to the use of these sequences in the diagnosis, treatment, and prevention of cancer and developmental disorders.

BACKGROUND OF THE INVENTION

LIM proteins are a family of proteins that share a common structural domain. The LIM motif is so named because it was first described in three proteins from *Drosophila melanogaster* designated L, I, and M. The LIM motif is a cysteine-rich region with a characteristic pattern: [C—X—X—C—$X_{17\pm1}$—H—X—X—C]—X—X—[C—X—X—C—$X_{17\pm1}$—C—X—X—C] (SEQ ID NO:4). LIM motifs form two loop structures and coordinate a zinc ion within each loop.

The LIM motif has been identified in a variety of proteins including transcription factors, cytoskeletal proteins, and signaling molecules. LIM proteins are involved in cell fate determination, growth regulation, and oncogenesis. At least twenty-three members of the LIM family have been described, from nematodes to humans. Some LIM proteins consist of one, two, or three repeats of the LIM motif and little else (LIM-only proteins). Others contain a LIM motif with a homeodomain (LIM-HD proteins) or a protein kinase domain (LIM-PK). LIM-PK inhibits the Ras oncogene-mediated differentiation of neural PC12 cells. LIM-HD proteins interact with DNA as well as bind to other proteins and are implicated in the control of differentiation of specific cell types. Studies in *C. elegans* demonstrated that LIM-HD proteins are involved in control of cell differentiation. Lin-11, a LIM-HD protein, controls the asymmetric cell divisions during vulval development, while Mec-3 is required for the differentiation of mechanosensory neurons (Way and Chalfie (1988) Cell 54:5–16; Freyd et al. (1990) Nature 344:876–879).

The LIM-only proteins have not been shown to bind DNA, although the LIM structure is similar to the zinc finger, a well-characterized DNA-binding domain. LIM-only proteins include the rat cysteine-rich intestinal protein (CRIP), the human RBTN1 and RBTN2 proteins, and the chicken zyxin protein (Higuchi et al (1997) Oncogene 14:1819–1825; Sanchez-Garcia and Rabbitts (1994) Trends Genet. 10:315–320; and Dawid et al (1995) C.R. Acad. Sci. 318:295–306). The genes for RBTN1 and RBTN2 are located on chromosome 11. Translocation mutations of chromosome 11 are associated with specific human T-cell acute leukemias. Transgenic expression of RBTN1 or RBTN2 produces leukemia and lymphoma in mice (McGuire et al (1992) Mol. Cell. Biol. 12:4186–4196; Fisch et al (1992) Oncogene 7:238 –2397).

A LIM-only protein, mouse testin, was recently cloned and characterized from a mouse testis germ cell library. Mouse testin contains three repeats of the LIM motif. Messenger RNA for mouse testin is widely distributed, with particularly strong signals in testis, kidney, and spleen (Divecha and Charleston (1995) Gene 156: 283–286).

The discovery of a new human testin and the polynucleotides encoding it satisfies a need in the art by providing new compositions which are useful in the diagnosis, treatment, and prevention of cancer and developmental disorders.

SUMMARY OF THE INVENTION

The invention features a substantially purified polypeptide, human testin (HTES), comprising a sequence of SEQ ID NO:1 or a fragment of SEQ ID NO:1.

The invention further provides a substantially purified variant of HTES having at least 90% amino acid identity to the sequence of SEQ ID NO:1 or a fragment of SEQ ID NO:1. The invention also provides an isolated and purified polynucleotide encoding the polypeptide comprising the sequence of SEQ ID NO:1 or a fragment of SEQ ID NO:1. The invention also includes an isolated and purified polynucleotide variant having at least 90% polynucleotide identity to the polynucleotide encoding the polypeptide comprising the sequence of SEQ ID NO:1 or a fragment of SEQ ID NO:1.

Additionally, the invention provides a composition comprising a polynucleotide encoding the polypeptide comprising the sequence of SEQ ID NO:1 or a fragment of SEQ ID NO:1. The invention further provides an isolated and purified polynucleotide which hybridizes under stringent conditions to the polynucleotide encoding the polypeptide comprising the sequence of SEQ ID NO:1 or a fragment of SEQ ID NO:1, as well as an isolated and purified polynucleotide which is complementary to the polynucleotide encoding the polypeptide comprising the sequence of SEQ ID NO:1 or a fragment of SEQ ID NO:1.

The invention also provides an isolated and purified polynucleotide comprising a sequence of SEQ ID NO:2 or a fragment of SEQ ID NO:2, and an isolated and purified polynucleotide variant having at least 90% polynucleotide identity to the polynucleotide comprising the sequence of SEQ ID NO:2 or a fragment of SEQ ID NO:2. The invention also provides an isolated and purified polynucleotide which is complementary to the polynucleotide comprising the sequence of SEQ ID NO:2 or a fragment of SEQ ID NO:2.

The invention further provides an expression vector containing at least a fragment of the polynucleotide encoding the polypeptide comprising the sequence of SEQ ID NO:1 or a fragment of SEQ ID NO:1. In another aspect, the expression vector is contained within a host cell.

The invention also provides a method for producing a polypeptide comprising a sequence of SEQ ID NO:1 or a fragment of SEQ ID NO:1, the method comprising the steps of: (a) culturing the host cell containing an expression vector containing at least a fragment of a polynucleotide encoding HTES under conditions suitable for the expression of the polypeptide; and (b) recovering the polypeptide from the host cell culture.

The invention also provides a pharmaceutical composition comprising a substantially purified HTES having the sequence of SEQ ID NO:1 or a fragment of SEQ ID NO:1 in conjunction with a suitable pharmaceutical carrier.

The invention provides a purified antibody which binds specifically to a polypeptide having the amino acid sequence of SEQ ID NO:1. The invention also provides a composition comprising the antibody which binds specifically to a polypeptide having the amino acid sequence of SEQ ID NO:1. The invention further provides methods for preparing polyclonal and monoclonal antibodies which bind specifically to a polypeptide having the amino acid sequence of SEQ ID NO:1. The invention still further provides for a chimeric antibody, a single chain antibody, a Fab fragment, and a F(ab')$_2$ fragment. The method yet still further provides for an antibody identified by screening a Fab expression library or a recombinant immunoglobulin library.

The invention provides a method for detecting a polypeptide having the amino acid sequence of SEQ ID NO:1 in a sample comprising combining the antibody which binds specifically to a polypeptide having the amino acid sequence of SEQ ID NO:1 with a sample under conditions to allow specific binding and detecting specific binding, wherein specific binding indicates the presence of polypeptide having the amino acid sequence of SEQ ID NO:1 in the sample. In different embodiments, the sample is from a subject with cancer of the uterus, prostate cancer, or breast cancer. The invention further provides a method for treating a cancer, the method comprising administering to a subject in need of such treatment an effective amount of an antibody which binds specifically to HTES.

The invention also provides a method for treating or preventing a developmental disorder, the method comprising administering to a subject in need of such treatment an effective amount of an antibody which specifically binds to HTES.

The invention still further provides a method of using an antibody to purify a polypeptide having the amino acid sequence of SEQ ID NO:1 from a sample by combining the antibody with a sample under conditions to allow specific binding and separating the antibody from the polypeptide, thereby obtaining purified polypeptide having the amino acid sequence of SEQ ID NO:1.

The invention also provides a method for detecting a polynucleotide encoding HTES in a biological sample containing nucleic acids, the method comprising hybridizing the complement of the polynucleotide encoding the polypeptide comprising the sequence of SEQ ID NO:1 or a fragment of SEQ ID NO:1 to at least one of the nucleic acids of the biological sample, thereby forming a hybridization complex and detecting the hybridization complex, wherein the presence of the hybridization complex correlates with the presence of a polynucleotide encoding HTES in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, 1D, 1E, and 1F show the amino acid sequence (SEQ ID NO:1) and nucleic acid sequence (SEQ ID NO:2) of HTES. The alignment was produced using MACDNASIS PRO software (Hitachi Software Engineering, South San Francisco Calif.).

FIGS. 2A and 2B show the amino acid sequence alignments between HTES (338680; SEQ ID NO:1), and mouse testin (GI 475210; SEQ ID NO:3), produced using the multisequence alignment program of LASERGENE software (DNASTAR, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"HTES" refers to the amino acid sequences of substantially purified HTES obtained from any species, particularly a mammalian species, including bovine, ovine, porcine, murine, equine, and preferably the human species, from any source, whether natural, synthetic, semi-synthetic, or recombinant.

"Agonist" refers to a molecule which, when bound to HTES, increases or prolongs the duration of the effect of HTES. Agonists may include proteins, nucleic acids, carbohydrates, or any other molecules which bind to and modulate the effect of HTES.

"Allele" is an alternative form of the gene encoding HTES. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HTES include those sequences with deletions, insertions, or substitutions of different nucleotides, resulting in a polynucleotide the same HTES or a polypeptide with at least one functional characteristic of HTES. Included within this definition are polymorphisms, which may or may not be readily detectable using a particular oligonucleotide probe of the polynucleotide encoding HTES, and improper or unexpected hybridization to alleles, with a locus other than the normal chromosomal locus for the polynucleotide sequence encoding HTES. The encoded protein may also be "altered" and may contain deletions, insertions, or substitutions of amino acid residues which produce a silent change and result in a functionally equivalent HTES. Deliberate amino acid substitutions may be made on the basis of similarity in polarity, charge, solubility, hydrophobicity, hydrophilicity, and/or the amphipathic nature of the residues, as long as the biological or immunological activity of HTES is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine;

asparagine and glutamine; serine and threonine; and phenylalanine and tyrosine.

"Amino acid" refers to an amino acid sequence, oligopeptide, peptide, polypeptide, or protein sequence, or a fragment of any of these, and to naturally occurring or synthetic molecules. In this context, "fragments", "immunogenic fragments", or "antigenic fragments" refer to fragments of HTES which are preferably about 5 to about 15 amino acids in length and which retain some biological activity or immunological activity of HTES.

"Amplification" relates to the production of additional copies of a nucleic acid sequence. Amplification is generally carried out using polymerase chain reaction (PCR) technologies well known in the art.

"Antagonist" refers to a molecule which, when bound to HTES, decreases the amount or the duration of the effect of the biological or immunological activity of HTES. Antagonists may include proteins, nucleic acids, carbohydrates, antibodies, or any other molecules which decrease the effect of HTES.

"Antibody" refers to intact molecules as well as to fragments thereof, such as Fab, $F(ab')_2$, and Fv fragments, which are capable of binding the epitopic determinant. Antibodies that bind HTES polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

"Antigenic determinant" refers to that fragment of a molecule, an epitope, that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen for binding to an antibody.

"Antisense" refers to any composition containing a nucleic acid sequence which is complementary to a specific nucleic acid sequence. The"antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

"Biologically active" refers to a protein having structural, regulatory, or biochemical functions of a naturally occurring molecule. Likewise, "immunologically active" refers to the capability of the natural, recombinant, or synthetic HTES, or of any oligopeptide thereof, to induce a specific immune response in appropriate animals or cells and to bind with specific antibodies.

"Complementary" refers to the natural binding of polynucleotides under permissive salt and temperature conditions by base pairing. For example, the sequence "A-G-T" binds to the complementary sequence "T-C-A." Complementarity between two single-stranded molecules may be "partial", such that only some of the nucleic acids bind, or it may be "complete", such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" refers broadly to any composition containing the given polynucleotide or amino acid sequence. The composition may comprise a dry formulation, an aqueous solution, or a sterile composition. Compositions comprising polynucleotide sequences encoding HTES or fragments of HTES may be employed as hybridization probes. The probes may be stored in freeze-dried form, or they may be associated with a stabilizing agent such as a carbohydrate. In hybridizations, the probe may be deployed in an aqueous solution containing salts, detergents, and other components such as Denhardt's solution, dry milk, salmon sperm DNA, and the like.

"Consensus sequence" refers to a nucleic acid sequence which has been resequenced to resolve uncalled bases, extended using XL-PCR kit (PE Biosystems, Foster City Calif.) in the 5' and/or the 3' direction and resequenced, or which has been assembled from the overlapping sequences of more than one Incyte Clone using a computer program for fragment assembly, such as the GELVIEW fragment assembly system (Genetics Computer Group, Madison Wis.). Some sequences have been both extended and assembled to produce the consensus sequence.

The phrase "correlates with expression of a polynucleotide" indicates that the detection of the presence of nucleic acids, the same or related to a nucleic acid sequence encoding HTES, by northern analysis is indicative of the presence of the expression of transcripts encoding HTES in a sample.

A "deletion" refers to a change in the amino acid or nucleotide sequence that results in the absence of one or more amino acid residues or nucleotides.

"Derivative" refers to the chemical modification of HTES, of a polynucleotide sequence encoding HTES, or of a polynucleotide sequence complementary to a polynucleotide sequence encoding HTES. Chemical modifications of a polynucleotide sequence can include replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

"Homology" refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

"Percent identity" refers to the percentage of sequence identity found in a comparison of two or more amino acid or nucleic acid sequences. Percent identity can be determined electronically using the MEGALIGN program (DNASTAR). This program can create alignments between two or more sequences using the clustal method. (Higgins and Sharp (1988) Gene 73:237–244). The clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent identity between nucleic acid sequences can also be calculated by the clustal method.

"Human artificial chromosomes" (HACs) are linear microchromosomes which may contain DNA sequences of about 6 kb to 10 Mb in size, and which contain all of the elements required for stable mitotic chromosome segregation and maintenance.

"Humanized antibody" refers to antibody molecules in which the amino acid sequence in the non-antigen binding regions has been altered so that the antibody more closely resembles a human antibody and retains its original binding ability.

"Hybridization" refers to any process by which a strand of nucleic acid binds with a complementary strand through base pairing. "Hybridization complex" refers to a complex formed between two nucleic acid sequences by formation of hydrogen bonds between complementary bases. A hybridization complex may be formed in solution or between one nucleic acid sequence present in solution and another nucleic acid sequence immobilized on a "substrate", the, paper, membranes, filters, chips, pins or glass slides, or any other appropriate surface to which cells or their nucleic acids have been fixed.

"Immune response" refers to conditions associated with inflammation, trauma, immune disorders, or infectious or genetic diseases, and the like. These conditions can be characterized by expression of various factors, such as cytokines, chemokines, and other signaling molecules, which may affect cellular and systemic defense.

"Insertion" refers to the addition of one or more amino acid residues or nucleotides, respectively, to the sequence found in the naturally occurring molecule.

"Microarray" refers to an arrangement of polynucleotides or oligonucleotides on a substrate.

"Modulate" refers to a change, increase or decrease, in protein activity, binding characteristics, or any other biological, functional, or immunological properties of HTES.

"Nucleic acid" refers to a nucleic acid sequence, oligonucleotide, nucleotide, polynucleotide, or any fragment thereof, to DNA or RNA of genomic or synthetic origin which may be single-stranded or double-stranded and may represent the sense or the antisense strand, to a PNA, or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

"Oligonucleotide" refers to a nucleic acid sequence of about 6 nucleotides to about 60 nucleotides, preferably about 15 to about 30 nucleotides, and most preferably about 20 to about 25 nucleotides, which can be used in PCR amplification, in a hybridization assay, or on a microarray. The term is substantially equivalent to "amplimer", "primer", and "oligomer" as commonly defined in the art.

"Peptide nucleic acid" refers to an antisense molecule or anti-gene agent which comprises an oligonucleotide of at least about 5 nucleotides in length linked to a peptide backbone of amino acid residues ending in a terminal lysine which confers solubility to the composition. PNAs preferentially bind complementary single stranded DNA and RNA and stop transcript elongation and may be pegylated to extend their lifespan in the cell.

"Sample" is used in its broadest sense. A sample suspected of containing nucleic acids encoding HTES, or fragments thereof, or HTES itself may comprise a bodily fluid; an extract from a cell, chromosome, organelle, or membrane isolated from a cell; a cell; genomic DNA, RNA, or cDNA (in solution or bound to a substrate); a tissue; a tissue print; and the like.

"Specific binding" refers to that interaction between a protein or peptide and an agonist, an antibody, or an antagonist. The interaction is dependent upon the presence of an epitope recognized by the binding molecule. For example, if an antibody is specific for epitope "A," the presence of a polypeptide containing the epitope A, or the presence of free unlabeled A, in a reaction containing free labeled A and the antibody will reduce the amount of labeled A that binds to the antibody.

"Stringent conditions" refers to conditions which permit hybridization between polynucleotide sequences and the claimed polynucleotide sequences. Suitably stringent conditions can be defined by GC content, the concentration of salt in the prehybridization and hybridization solutions, and by the hybridization temperature; they are well known in the art. In particular, stringency can be increased by reducing the concentration of salt, or raising the hybridization temperature. In particular, hybridization would occur under high stringency conditions at 42° C. in 50% formamide, 5×SSPE, 0.3% SDS, and 200 $\mu$g/ml sheared and denatured salmon sperm DNA.

"Substantially purified" refers to nucleic acid or amino acid sequences that are removed from their natural environment and are isolated or separated, and are at least about 60% free, preferably about 75% free, and most preferably about 90% free from other components with which they naturally occur.

A "substitution" is the replacement of one or more amino acids or nucleotides by different amino acids or nucleotides, respectively.

"Transformation" describes a process by which exogenous DNA enters and changes a recipient cell. Transformation may occur under natural or artificial conditions according to various methods well known in the art and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, and refers to cells which transiently express the inserted DNA or RNA for limited periods of time.

A "variant" refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art such as LASERGENE software (DNASTAR).

The Invention

The invention is based on the discovery of a new human testin (HTES), the polynucleotides encoding HTES, and the use of these compositions for the diagnosis, treatment, or prevention of cancer and developmental disorders.

Nucleic acids encoding the HTES of the present invention were first identified in Incyte Clone 338680 from the granulocyte cDNA library (NEUTFMT01) using a computer search for amino acid sequence alignments. A consensus sequence, SEQ ID NO:2, was derived from the following overlapping and/or extended nucleic acid sequences: Incyte Clones 338680 (NEUTFMT01), 351012 (CONCNOT01), 1333542 (COLNNOT13), 1752762 (LIVRTUT01), and 2230457 and 2230635 (PROSNOT16). Northern analysis shows the expression of this sequence in reproductive, cardiovascular, and gastrointestinal cDNA libraries, at least 58% of which are associated with cancer and 22% of which are associated with fetal tissue or proliferating cells. Of particular note is the expression of HTES in cancerous reproductive tissues including prostate, testicle, uterus and breast.

In one embodiment, the invention encompasses a polypeptide comprising the amino acid sequence of SEQ ID NO:1, as shown in FIGS. 1A–1F. HTES is 421 amino acids in length and has a LIM domain signature sequence, from $C_{236}$ through $L_{275}$. In addition, HTES has two cytochrome C family heme-binding site signature sequences, from $C_{268}$ through $E_{273}$ and from $C_{361}$ through $N_{366}$, two potential N-glycosylation sites at $N_{103}$ and $N_{379}$, a potential cAMP- and cGMP-dependent phosphorylation site at $S_{421}$, five potential casein kinase II phosphorylation sites at $S_{56}$, $S_{168}$, $S_{242}$, $T_{270}$, and $T_{314}$, two potential protein kinase C phosphorylation sites at $S_{168}$ and $S_{296}$, and a potential tyrosine kinase phosphorylation site at $Y_{71}$. As shown in FIGS. 2A and 2B, HTES has chemical and structural homology with mouse testin (GI 475210; SEQ ID NO:3). In particular, HTES and mouse testin share 83% identity. In addition, HTES and mouse testin share a cytochrome c family heme-binding domain, a LIM domain signature sequence, and several phosphorylation sites.

The invention also encompasses HTES variants. A preferred HTES variant is one which has at least about 80%, more preferably at least about 90%, and most preferably at least about 95% amino acid sequence identity to the HTES amino acid sequence, and which contains at least one functional or structural characteristic of HTES.

The invention also encompasses polynucleotides which encode HTES. In a particular embodiment, the invention encompasses a polynucleotide sequence comprising the sequence of SEQ ID NO:2, which encodes an HTES.

The invention also encompasses a variant of a polynucleotide sequence encoding HTES. In particular, such a variant polynucleotide sequence will have at least about 80%, more preferably at least about 90%, and most preferably at least about 95% polynucleotide sequence identity to the polynucleotide sequence encoding HTES. A particular aspect of the invention encompasses a variant of SEQ ID NO:2 which has at least about 80%, more preferably at least about 90%, and most preferably at least about 95% polynucleotide sequence identity to SEQ ID NO:2. Any one of the polynucleotide variants described above can encode an amino acid sequence which contains at least one functional or structural characteristic of HTES.

It will be appreciated by those skilled in the art that as a result of the degeneracy of the genetic code, a multitude of polynucleotide sequences encoding HTES, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HTES, and all such variations are to be considered as being specifically disclosed.

Although nucleotide sequences which encode HTES and its variants are preferably capable of hybridizing to the nucleotide sequence of the naturally occurring HTES under appropriately selected conditions of stringency, it may be advantageous to produce nucleotide sequences encoding HTES or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HTES and its derivatives without altering the encoded amino acid sequences include the production of RNA transcripts having more desirable properties, such as a greater half-life, than transcripts produced from the naturally occurring sequence.

The invention also encompasses production of DNA sequences which encode HTES and HTES derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HTES or any fragment thereof.

Also encompassed by the invention are polynucleotide sequences that are capable of hybridizing to the claimed polynucleotide sequences, and, in particular, to those shown in SEQ ID NO:2, or a fragment of SEQ ID NO:2, under various conditions of stringency. (See, e.g., Wahl and Berger (1987) Methods Enzymol. 152:399–407; and Kimmel (1987) Methods Enzymol. 152:507–511.)

Methods for DNA sequencing are well known and generally available in the art and may be used to practice any of the embodiments of the invention. The methods may employ such enzymes as the Klenow fragment of DNA polymerase I, T7 SEQUENASE DNA polymerase, Taq DNA polymerase, and THERMOSEQUENASE DNA polymerase (Amersham Pharmacia Biotech (APB), Picataway N.J.), or combinations of polymerases and proofreading exonucleases such as those found in the ELONGASE amplification system (Life Technologies, Gaithersburg Md.). Preferably, the process is automated with machines such as the MICROLAB 2200 system (Hamilton, Reno Nev.), DNA ENGINE thermal cycler (PTC200; MJ Research, Watertown Mass.) and the ABI CATALYST and the ABI PRISM 373 and 377 DNA sequencing systems (PE Biosystems).

The nucleic acid sequences encoding HTES may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus (Sarkar (1993) PCR Methods Applic. 2:318–322). In particular, genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, et al. (1988) Nucleic Acids Res. 16:8186). The primers may be designed using commercially available software such as OLIGO 4.06 software (National Biosciences, Plymouth Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA. (See, e.g., Lagerstrom et al. (1991) PCR Methods Applic. 1:111–119.) In this method, multiple restriction enzyme digestions and ligations may be used to place an engineered double-stranded sequence into an unknown fragment of the DNA molecule before performing PCR. Other methods which may be used to retrieve unknown sequences are known in the art. (See, e.g., Parker et al. (1991) Nucleic Acids Res. 19:3055–3060.) Additionally, one may use PCR, nested primers, and PROMOTERFINDER libraries (Clontech, Palo Alto, Calif.) to walk genomic DNA. This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., GENOTYPER and SEQUENCE NAVIGATOR software, PE Biosystems), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HTES may be used in recombinant DNA molecules to direct expression of HTES, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HTES.

As will be understood by those of skill in the art, it may be advantageous to produce HTES-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HTES encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HTES may be ligated to a heterologous sequence to encode a fusion protein. For example, to screen peptide libraries for inhibitors of HTES activity, it may be useful to encode a chimeric HTES protein that can be recognized by a commercially available antibody. A fusion protein may also be engineered to contain a cleavage site located between the HTES encoding sequence and the heterologous protein sequence, so that HTES may be cleaved and purified away from the heterologous moiety.

In another embodiment, sequences encoding HTES may be synthesized, in whole or in part, using chemical methods well known in the art. (See, e.g., Caruthers et al. (1980) Nucleic Acids Symp. Ser. (7) 215–223, and Horn et al. (1 980) Nucleic Acids Symp. Ser. (7) 225–232.) Alternatively, the protein itself may be produced using chemical methods to synthesize the amino acid sequence of HTES, or a fragment thereof. For example, peptide synthesis can be performed using various solid-phase techniques. (Roberge et al. (1995) Science 269:202–204.) Automated synthesis may be achieved using the ABI 431A peptide synthesizer (PE Biosystems).

The newly synthesized peptide may be substantially purified by preparative high performance liquid chromatography. (See, e.g, Chiez and Regnier (1990) Methods Enzymol. 182:392421.) The composition of the synthetic peptides may be confirmed by amino acid analysis or by sequencing. (See, e.g., Creighton (1983) *Proteins, Structures and Molecular Properties,* W H Freeman, New York N.Y.) Additionally, the amino acid sequence of HTES, or any part thereof, may be altered during direct synthesis and/or combined with sequences from other proteins, or any part thereof, to produce a variant polypeptide.

In order to express a biologically active HTES, the nucleotide sequences encoding HTES or derivatives thereof may be inserted into appropriate expression vector, i.e., a vector which contains the necessary elements for the transcription and translation of the inserted coding sequence.

Methods which are well known to those skilled in the art may be used to construct expression vectors containing sequences encoding HTES and appropriate transcriptional and translational control elements. These methods include in vitro recombinant DNA techniques, synthetic techniques, and in vivo genetic recombination. (See, e.g., Sambrook et al. (1989) *Molecular Cloning, A Laboratory Manual,* Cold Spring Harbor Press, Plainview N.Y., ch. 4, 8, and 16–17; and Ausubel et al. (1995, and periodic supplements) *Current Protocols in Molecular Biology,* John Wiley & Sons, New York N.Y., ch. 9, 13, and 16.)

A variety of expression vector/host systems may be utilized to contain and express sequences encoding HTES. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

The "control elements" or "regulatory sequences" are those non-translated regions of the vector (i.e., enhancers, promoters, and 5' and 3' untranslated regions) which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, La Jolla Calif.) or pSPORT1 plasmid (Life Technologies), and the like, may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HTES, vectors based on SV40 or EBV may be used with an appropriate selectable marker.

In bacterial systems, a number of expression vectors may be selected depending upon the use intended for HTES. For example, when large quantities of HTES are needed for the induction of antibodies, vectors which direct high level expression of fusion proteins that are readily purified may be used. Such vectors include, but are not limited to, multifunctional *E. coli* cloning and expression vectors such as BLUESCRIPT phagemid (Stratagene), in which the sequence encoding HTES may be ligated into the vector in frame with sequences for the amino-terminal Met and the subsequent 7 residues of β-galactosidase so that a hybrid protein is produced, pIN vectors (Van Heeke and Schuster (1989) J. Biol. Chem. 264:5503–5509). pGEX vectors (APB) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae,* a number of vectors containing constitutive or inducible promoters such as alpha factor, alcohol oxidase, and PGH, may be used. (See, e.g., Ausubel, supra; and Grant et al. (1987) Methods Enzymol. 153:516–544.)

In cases where plant expression vectors are used, the expression of sequences encoding HTES may be driven by any of a number of promoters. For example, viral promoters such as the 35S and 19S promoters of CaMV may be used alone or in combination with the omega leader sequence from TMV (Takamatsu (1987) EMBO J. 6:307–311). Alternatively, plant promoters such as the small subunit of RUBISCO or heat shock promoters may be used (Coruzzi et al. (1984) EMBO J. 3:1671–1680; Broglie et al. (1984) Science 224:838–843; and Winter et al. (1991) Results Probl. Cell Differ. 17:85–105). These constructs can be introduced into plant cells by direct DNA or pathogen-mediated transformation. Such techniques are described in a number of generally available reviews. (See, e.g., Hobbs or Murry In: *McGraw Hill Yearbook of Science and Technology* (1992) McGraw Hill, New York N.Y., pp. 191–196.)

An insect system may also be used to express HTES. For example, in one such system, *Autographa californica* nuclear polyhedrosis virus (AcNPV) is used as a vector to express foreign genes in *Spodoptera frugiperda* cells or in *Trichoplusia larvae.* The sequences encoding HTES may be cloned into a non-essential region of the virus, such as the polyhedrin gene, and placed under control of the polyhedrin promoter. Successful insertion of HTES will render the polyhedrin gene inactive and produce recombinant virus lacking coat protein. The recombinant viruses may then be used to infect, for example, *S. frugiperda* cells or *Trichoplusia larvae* in which HTES may be expressed. (See, e.g., Engelhard et al. (1994) Proc. Natl. Acad. Sci. 91:3224–3227.)

In mammalian host cells, a number of viral-based expression systems may be utilized. In cases where an adenovirus is used as an expression vector, sequences encoding HTES may be ligated into an adenovirus transcription/translation complex consisting of the late promoter and tripartite leader sequence. Insertion in a non-essential E1 or E3 region of the viral genome may be used to obtain a viable virus which is capable of expressing HTES in infected host cells (Logan and Shenk (1984) Proc. Natl. Acad. Sci. 81:3655–3659). In addition, transcription enhancers, such as the Rous sarcoma virus (RSV) enhancer, may be used to increase expression in mammalian host cells.

HACs may also be employed to deliver larger fragments of DNA than can be contained and expressed in a plasmid. HACs are constructed and delivered via conventional delivery methods (liposomes, polycationic amino polymers, or vesicles) for therapeutic purposes.

Specific initiation signals may also be used to achieve more efficient translation of sequences encoding HTES. Such signals include the ATG initiation codon and adjacent sequences. In cases where sequences encoding HTES and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used. (See, e.g., Scharf et al. (1994) Results Probl. Cell Differ. 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and WI38), are available from the American Type Culture Collection (Manassas Va.) and may be chosen to ensure the correct modification and processing of the foreign protein.

For long term, high yield production of recombinant proteins, stable expression is preferred. For example, cell lines capable of stably expressing HTES can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes and adenine phosphoribosyltransferase genes, which can be employed in tk$^-$ or apr$^-$ cells, respectively. (See, e.g., Wigler et al. (1977) Cell 11:223–232; Lowy et al. (1980) Cell 22:817–823) Also, antimetabolite, antibiotic, or herbicide resistance can be used as the basis for selection. For example, dhfr confers resistance to methotrexate; npt confers resistance to the aminoglycosides, neomycin and G-418; and als or pat confer resistance to chlorsulfuron and phosphinotricin acetyltransferase, respectively. (See, e.g., Wigler et al. (1980) Proc. Natl. Acad. Sci. 77:3567–3570; Colbere-Garapin et al (1981) J. Mol. Biol. 150:1–14; and Murry, supra.) Additional selectable genes have been described, e.g., trpB, which allows cells to utilize indole in place of tryptophan, or hisD, which allows cells to utilize histinol in place of histidine. (See, e.g., Hartman and Mulligan (1988) Proc. Natl. Acad. Sci. 85:8047–8051.) Recently, the use of visible markers has gained popularity with such markers as anthocyanins, β glucuronidase and its substrate GUS, and luciferase and its substrate luciferin. These markers can be used not only to identify transformants, but also to quantify the amount of transient or stable protein expression attributable to a specific vector system. (See, e.g., Rhodes et al. (1995) Methods Mol. Biol. 55:121–131.)

Although the presence/absence of marker gene expression suggests that the gene of interest is also present, the presence and expression of the gene may need to be confirmed. For example, if the sequence encoding HTES is inserted within a marker gene sequence, transformed cells containing sequences encoding HTES can be identified by the absence of marker gene function. Alternatively, a marker gene can be placed in tandem with a sequence encoding HTES under the control of a single promoter. Expression of the marker gene in response to induction or selection usually indicates expression of the tandem gene as well.

Alternatively, host cells which contain the nucleic acid sequence encoding HTES and express HTES may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein sequences.

The presence of polynucleotide sequences encoding HTES can be detected by DNA-DNA or DNA-RNA hybridization or amplification using probes or fragments or fragments of polynucleotides encoding HTES. Nucleic acid amplification based assays involve the use of oligonucleotides or oligomers based on the sequences encoding HTES to detect transformants containing DNA or RNA encoding HTES.

A variety of protocols for detecting and measuring the expression of HTES, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HTES is preferred, but a competitive binding assay may be employed. These and other assays are well described in the art. (See, e.g., Hampton et al. (1990) *Serological Methods, a Laboratory Manual,* APS Press, St Paul Minn., Section IV; and Maddox et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HTES include oligolabeling, nick translation, end-labeling, or PCR amplification using a labeled nucleotide. Alternatively, the sequences encoding HTES, or any fragments thereof, may be cloned into a vector for the production of an MRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by APB and Promega (Madison Wis.). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HTES may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HTES may be designed to contain signal sequences which direct secretion of HTES through a prokaryotic or eukaryotic cell membrane. Other constructions may be used to join sequences encoding HTES to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex, Seattle WA). The inclusion of cleavable linker sequences, such as those specific for Factor XA or enterokinase (Invitrogen, San Diego Calif.), between the purification domain and the HTES encoding sequence may be used to facilitate purification. One such expression vector provides for expression of a fusion protein containing HTES and a nucleic acid encoding 6 histidine residues preceding a thioredoxin or an enterokinase cleavage site. The histidine residues facilitate purification on immobilized metal ion affinity chromatography (IMAC; Porath et al. (1992) Prot. Exp. Purif. 3:263–281). The enterokinase cleavage site provides a means for purifying HTES from the fusion protein (Kroll et al. (1993) DNA Cell Biol. 12:441453).

Fragments of HTES may be produced not only by recombinant production, but also by direct peptide synthesis using solid-phase techniques (Merrifield (1963) J. Am. Chem. Soc. 85:2149–2154). Protein synthesis may be performed by manual techniques or by automation. Automated synthesis may be achieved, for example, using the ABI 431A peptide synthesizer (PE Biosystems). Various fragments of HTES may be synthesized separately and then combined to produce the full length molecule.

Therapeutics

Chemical and structural homology exists between HTES and mouse testin (GI 475210). In addition, HTES is expressed in cancerous and in proliferating or fetal tissues. Therefore, HTES appears to play a role in cancer and developmental disorders.

Therefore, in one embodiment, an antagonist of HTES may be administered to a subject to treat or prevent a cancer. Such a cancer may include, but is not limited to, adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, nerve, ovary, pancreas, parathyroid, penis, prostate, salivary glands, skin, spleen, testis, thymus, thyroid, and uterus. In one aspect, an antibody which specifically binds HTES may be used directly as an antagonist or indirectly as a targeting or delivery mechanism for bringing a pharmaceutical agent to cells or tissue which express HTES.

In an additional embodiment, a vector expressing the complement of the polynucleotide encoding HTES may be administered to a subject to treat or prevent a cancer including, but not limited to, those described above.

In a further embodiment, an antagonist of HTES may be administered to a subject to treat or prevent a developmental disorder. Such a disorder may include, but is not limited to, renal tubular acidosis, anemia, Cushing's syndrome, achondroplastic dwarfism, Duchenne and Becker muscular dystrophy, epilepsy, gonadal dysgenesis, WAGR syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spinal bifida, and congenital glaucoma, cataract, or sensorineural hearing loss. In one aspect, an antibody which specifically binds HTES may be used directly as an antagonist or indirectly as a targeting or delivery mechanism for bringing a pharmaceutical agent to cells or tissue which express HTES.

In an additional embodiment, a vector expressing the complement of the polynucleotide encoding HTES may be administered to a subject to treat or prevent a developmental disorder, including, but not limited to, those described above.

In yet another embodiment, a substantially purified HTES or fragment thereof, a vector capable of expressing HTES or fragment thereof, or an agonist which modulates the activity of HTES, may be administered to a subject to treat or prevent an immunodeficiency. Such an immunodeficieny may include, but is not limited to agammaglobinemia of Bruton, common variable immunodeficiency, DiGeorge's syndrome (thymic hypoplasia), isolated IgA deficiency, severe combined immunodeficiency diseases, and immunodeficiency with thrombocytopenia and eczema (Wiskott-Aldrich syndrome), and immunodeficiency due to cytoablative therapy.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HTES may be produced using methods which are generally known in the art. In particular, purified HTES may be used to produce antibodies or to screen libraries of pharmaceutical agents to identify those which specifically bind HTES. Antibodies to HTES may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with HTES or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HTES have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HTES amino acids may be fused with those of another protein, such as KLH, and antibodies to the chimeric molecule may be produced.

Monoclonal antibodies to HTES may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler et al. (1975) Nature 256:495–497; Kozbor et al. (1985) J. Immunol. Methods 81:31–42; Cote et al. (1983) Proc. Natl. Acad. Sci. 80:2026–2030; and Cole et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison et al. (1984) Proc. Natl. Acad. Sci. 81:6851–6855; Neuberger et al. (1984) Nature 312:604–608; and Takeda et al. (1985) Nature 314:452–454.) Alternatively, techniques described for the production of single chain antibodies may be adapted, using methods known in the art, to produce HTES-specific single chain antibodies. Antibodies with related specificity, but of distinct idiotypic composition, may be generated by chain shuffling from random combinatorial immunoglobulin libraries. (See, e.g., Burton (1991) Proc. Natl. Acad. Sci. 88:11120–11123.)

Antibodies may also be produced by inducing in vivo production in the lymphocyte population or by screening immunoglobulin libraries or panels of highly specific binding reagents as disclosed in the literature (Orlandi et al. (1989) Proc. Natl. Acad. Sci. 86:3833–3837; Winter et al. (1991) Nature 349:293–299).

Antibody fragments which contain specific binding sites for HTES may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse et al. (1989) Science 254:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HTES and its specific antibody. A two-site, monoclonal-based immunoassay utilizing monoclonal antibodies reactive to two non-interfering HTES epitopes is preferred, but a competitive binding assay may also be employed. (Maddox, supra.)

In another embodiment of the invention, the polynucleotides encoding HTES, or any fragment or complement thereof, may be used for therapeutic purposes. In one aspect, the complement of the polynucleotide encoding HTES may be used in situations in which it would be desirable to block the transcription of the mRNA. In particular, cells may be transformed with sequences complementary to polynucleotides encoding HTES. Thus, complementary molecules or fragments may be used to modulate HTES activity, or to achieve regulation of gene function. Such technology is now well known in the art, and sense or antisense oligonucleotides or larger fragments can be designed from various locations along the coding or control regions of sequences encoding HTES.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequence complementary to the polynucleotides of the gene encoding HTES. (See, e.g., Sambrook, supra; and Ausubel, supra.)

Genes encoding HTES can be turned off by transforming a cell or tissue with expression vectors which express high levels of a polynucleotide or fragment thereof encoding HTES. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HTES. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in Gee et al. (In: Huber and Carr (1994) *Molecular and Immunologic Approaches,* Futura Publishing, Mt. Kisco N.Y., pp. 163–177). A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules specifically and efficiently catalyze endonucleolytic cleavage of sequences encoding HTES.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HTES. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art (Goldman et al. (1997) Nature Biotechnol. 15:462–466).

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HTES, antibodies to HTES, and mimetics, agonists, antagonists, or inhibitors of HTES. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intraarterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethylcellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethylcellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acid. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HTES, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays of neoplastic cells, for example, or in animal models, usually mice, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HTES or fragments thereof, antibodies of HTES, and agonists, antagonists or inhibitors of HTES, which ameliorates the symptoms or condition. Therapeutic efficacy and toxicity may be determined by standard pharmaceutical procedures in cell cultures or with experimental animals, such as by calculating the ED50 (the dose therapeutically effective in 50% of the population) or LD50 (the dose lethal to 50% of the population) statistics. The dose ratio between toxic and therapeutic effects is the therapeutic index, and it can be expressed as the LD50/ED50 ratio. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on the half-life and clearance rate of the particular formulation.

Normal dosage amounts may vary from 0.1 $\mu$g to 100,000 $\mu$g, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HTES may be used for the diagnosis of disorders characterized by expression of HTES, or in assays to monitor patients being treated with HTES or agonists, antagonists, and inhibitors of HTES. Antibodies useful for diagnostic purposes may be prepared in the same manner as those described above for therapeutics. Diagnostic assays for HTES include methods which utilize the antibody and a label to detect HTES in human body fluids or in extracts of cells or tissues. The antibodies may be used with or without modification, and may be labeled by covalent or non-covalent joining with a reporter molecule. A wide variety of reporter molecules, several of which are described above, are known in the art and may be used.

A variety of protocols for measuring HTES, including ELISAs, RIAs, and FACS, are known in the art and provide a basis for diagnosing altered or abnormal levels of HTES expression. Normal or standard values for HTES expression are established by combining body fluids or cell extracts taken from normal mammalian subjects, preferably human, with antibody to HTES under conditions suitable for complex formation. The amount of standard complex formation may be quantified by various methods, preferably by photometric means. Quantities of HTES expressed in subject and disease samples from biopsied tissues are compared with the standard values. Deviation between standard and subject values establishes the parameters for diagnosing disease.

In another embodiment of the invention, the polynucleotides encoding HTES may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HTES may be correlated with disease. The diagnostic assay may be used to distinguish between absence, presence, and excess expression of HTES, and to monitor regulation of HTES levels during therapeutic intervention.

In one aspect, hybridization with PCR probes which are capable of detecting polynucleotide sequences, including genomic sequences, encoding HTES or closely related molecules may be used to identify nucleic acid sequences which encode HTES. The specificity of the probe, whether it is made from a highly specific region (e.g., the 5' regulatory region) or from a less specific region (e.g., the 3' coding region), and the stringency of the hybridization or amplification (maximal, high, intermediate, or low), will determine whether the probe identifies only naturally occurring sequences encoding HTES, alleles, or related sequences.

Probes may also be used for the detection of related sequences, and should preferably contain at least 50% of the nucleotides from any of the HTES encoding sequences. The hybridization probes of the subject invention may be DNA or RNA and may be derived from the sequence of SEQ ID NO:2 or from genomic sequences including promoter and enhancer elements and introns of the naturally occurring HTES.

Means for producing specific hybridization probes for DNAs encoding HTES include the cloning of polynucleotide sequences encoding HTES or HTES derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}$p or $^{35}$S, or by enzymatic labels, such as alkaline phosphatase coupled to the probe via avidin/biotin coupling systems, and the like.

Polynucleotide sequences encoding HTES may be used for the diagnosis of a disorder associated with expression of HTES. Examples of such a disorder include, but are not limited to, cancer, such as adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, nerve, ovary, pancreas, parathyroid, penis, prostate, salivary glands, skin, spleen, testis, thymus, thyroid, and uterus, developmental disorders, such as renal tubular acidosis, anemia, Cushing's syndrome, achondroplastic dwarfism, Duchenne and Becker muscular dystrophy, epilepsy, gonadal dysgenesis, WAGR syndrome, myelodysplastic syndrome, hereditary mucoepithelial dysplasia, hereditary keratodermas, hereditary neuropathies such as Charcot-Marie-Tooth disease and neurofibromatosis, hypothyroidism, hydrocephalus, seizure disorders such as Syndenham's chorea and cerebral palsy, spinal bifida, and congenital glaucoma, cataract, or sensorineural hearing loss, and immunodeficiencies, such as agammaglobinemia of Bruton, common variable immunodeficiency, DiGeorge's syndrome (thymic hypoplasia), isolated IgA deficiency, severe combined immunodeficiency diseases, and immunodeficiency with thrombocytopenia and eczema (Wiskott-Aldrich syndrome), and immunodeficiency due to cytoablative therapy. The polynucleotide sequences encoding HTES may be used in Southern or northern analysis, dot blot, or other membrane-based technologies; in PCR technologies; in dipstick, pin, and ELISA-like assays; and in microarrays utilizing fluids or tissues from patient biopsies to detect altered HTES expression. Such qualitative or quantitative methods are well known in the art.

In a particular aspect, the nucleotide sequences encoding HTES may be useful in assays that detect the presence of associated disorders, particularly those mentioned above. The nucleotide sequences encoding HTES may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered from that of a comparable control sample, the nucleotide sequences have hybridized with nucleotide sequences in the sample, and the presence of altered levels of nucleotide sequences encoding HTES in the sample indicates the presence of the associated disorder. Such assays may also be used to evaluate the efficacy of a particular therapeutic treatment regimen in animal studies, in clinical trials, or in monitoring the treatment of an individual patient.

In order to provide a basis for the diagnosis of a disorder associated with expression of HTES, a normal or standard profile for expression is established. This may be accomplished by combining body fluids or cell extracts taken from normal subjects, either animal or human, with a sequence, or a fragment thereof, encoding HTES, under conditions suitable for hybridization or amplification. Standard hybridization may be quantified by comparing the values obtained from normal subjects with values from an experiment in which a known amount of a substantially purified polynucleotide is used. Standard values obtained from normal samples may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to evaluate whether the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HTES may involve the use of PCR. These oligomers may be chemically synthesized, generated enzymatically, or produced in vitro. Oligomers will preferably contain a fragment of a polynucleotide encoding HTES, or a fragment of a polynucleotide complementary to the polynucleotide encoding HTES, and will be employed under optimized conditions for identification of a specific gene or condition. Oligomers may also be employed under less stringent conditions for detection or quantitation of closely related DNA or RNA sequences.

Methods which may also be used to quantitate the expression of HTES include radiolabeling or biotinylating nucleotides, coamplification of a control nucleic acid, and interpolating results from standard curves (Melby et al. (1993) J. Immunol. Methods 159:235–244; Duplaa et al. (1993) Anal. Biochem. 229–236). The speed of quantitation of multiple samples may be accelerated by running the assay in an ELISA-like format where the oligomer of interest is presented in various dilutions and a spectrophotometric or colorimetric response gives rapid quantitation.

In further embodiments, oligonucleotides or longer fragments derived from any of the polynucleotide sequences may be used as targets in a microarray. The microarray can be used to monitor the expression level of large numbers of genes simultaneously (to produce a transcript image) and to identify genetic variants, mutations, and polymorphisms. This information may be used in determining gene function, in understanding the genetic basis of a disorder, in diagnosing a disorder, and in developing and monitoring the activities of therapeutic agents.

In one embodiment, the microarray is prepared and used according to methods known in the art. (See, e.g., Chee et al. (1995) PCT application WO95/11995; Lockhart et al. (1996) Nature Biotechnol. 14:1675–1680; and Schena et al. (1996) Proc. Natl. Acad. Sci. 93:10614–10619.)

The microarray is preferably composed of a large number of unique single-stranded nucleic acid sequences, usually either synthetic antisense oligonucleotides or fragments of cDNAs, fixed to a substrate. The oligonucleotides are preferably about 6 to 60 nucleotides in length, more preferably about 15 to 30 nucleotides in length, and most preferably about 20 to 25 nucleotides in length. For a certain type of microarray, it may be preferable to use oligonucleotides which are about 7 to 10 nucleotides in length. The microarray may contain oligonucleotides which cover the known 5' or 3' sequence, or may contain sequential oligonucleotides which cover the full length sequence or unique oligonucleotides selected from particular areas along the length of the sequence. Polynucleotides used in the microarray may be oligonucleotides specific to a gene or genes of interest in which at least a fragment of the sequence is known or oligonucleotides specific to one or more unidentified cDNAs common to a particular cell or tissue type or to a normal, developmental, or disease state. In certain situations, it may be appropriate to use pairs of oligonucleotides on a microarray. The pairs will be identical, except for one nucleotide preferably located in the center of the sequence. The second oligonucleotide in the pair (mismatched by one) serves as a control. The number of oligonucleotide pairs may range from about 2 to 1,000,000.

In order to produce oligonucleotides to a known sequence for a microarray, the gene of interest is examined using a computer algorithm which starts at the 5' end, or, more preferably, at the 3' end of the nucleotide sequence. The algorithm identifies oligomers of defined length that are unique to the gene, have a GC content within a range suitable for hybridization, and lack predicted secondary structure that may interfere with hybridization. In one aspect, the oligomers are synthesized at designated areas on a substrate using a light-directed chemical process. The substrate may be paper, nylon, any other type of membrane, filter, chip, glass slide, or any other suitable substrate.

In one aspect, the oligonucleotides may be synthesized on the surface of the substrate by using a chemical coupling procedure and an ink jet application apparatus as described in Baldeschweiler et al. (1995; WO95/251116). In another aspect, a grid array analogous to a dot or slot blot may be used to arrange and link cDNA fragments or oligonucleotides to the surface of a substrate using a vacuum system or thermal, UV, mechanical or chemical bonding procedures. In yet another aspect, an array may be produced by hand or by using available devices, materials, and machines including multichannel pipettes or robotic instruments, and may contain 8, 24, 96, 384, 1536, or 6144 oligonucleotides, or any other multiple from 2 to 1,000,000 which lends itself to the efficient use of commercially available instrumentation.

In order to conduct sample analysis using the microarrays, polynucleotides are extracted from a biological sample. The biological samples may be obtained from any bodily fluid (blood, urine, saliva, phlegm, gastric juices, etc.), cultured cells, biopsies, or other tissue preparations. To produce probes, the polynucleotides extracted from the sample are used to produce nucleic acid sequences which are complementary to the nucleic acids on the microarray. If the microarray consists of cDNAs, antisense RNAs (aRNA) are appropriate probes. Therefore, in one aspect, mRNA is used to produce cDNA which, in turn and in the presence of fluorescent nucleotides, is used to produce fragment or oligonucleotide aRNA probes. These fluorescently labeled probes are incubated with the microarray so that the probe sequences hybridize to the cDNA oligonucleotides of the microarray. In another aspect, nucleic acid sequences used as probes can include polynucleotides, fragments, and complementary or antisense sequences produced using restriction enzymes, PCR technologies, and labeling kits well known in the area of hybridization technology.

Incubation conditions are adjusted so that hybridization occurs with precise complementary matches or with various degrees of less complementarity. After removal of nonhybridized probes, a scanner is used to determine the levels and patterns of fluorescence. The scanned images are examined to determine the degree of complementarity and the relative abundance of each oligonucleotide sequence on the microarray. A detection system may be used to measure the absence, presence, and amount of hybridization for all of the distinct sequences simultaneously. This data may be used for large scale correlation studies or for functional analysis of the sequences, mutations, variants, or polymorphisms among samples. (See, e.g., Heller et al. (1997) Proc. Natl. Acad. Sci. 94:2150–2155.)

In another embodiment of the invention, nucleic acid sequences encoding HTES may be used to generate hybridization probes useful for mapping the naturally occurring genomic sequence. The sequences may be mapped to a particular chromosome, to a specific region of a chromosome, or to artificial chromosome constructions such as HACs, yeast artificial chromosomes (YACs), bacterial artificial chromosomes (BACs), bacterial P1 constructions, or single chromosome cDNA libraries. (See, e.g., Price (1993) Blood Rev. 7:127–134; and Trask (1991) Trends Genet. 7:149–154.)

Fluorescent in situ hybridization (FISH) may be correlated with other physical chromosome mapping techniques and genetic map data. (See, e.g., Heinz-Ulrich et al. In: Meyers (1995) *Molecular Biology and Biotechnology*, VCH Publishers, New York N.Y., pp. 965–968.) Examples of genetic map data can be found in various scientific journals or at the Online Mendelian Inheritance in Man (OMIM) site. Correlation between the location of the gene encoding HTES on a physical chromosomal map and a specific disorder, or predisposition to a specific disorder, may help define the region of DNA associated with that disorder. The nucleotide sequences of the subject invention may be used to detect differences in gene sequences between normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, e.g., AT to 11q22–23, any sequences mapping to that area may represent associated or regulatory genes for further investigation (Gatti et al. (1988) Nature 336:577–580). The nucleotide sequence of the subject invention may also be used to detect differences in the chromosomal location due to translocation, inversion, etc., among normal, carrier, or affected individuals.

In another embodiment of the invention, HTES, its catalytic or immunogenic fragments, or oligopeptides thereof can be used for screening libraries of compounds in any of a variety of drug screening techniques. The fragment employed in such screening may be free in solution, affixed to a substrate, borne on a cell surface, or located intracellularly. The formation of binding complexes between HTES and the agent being tested may be measured.

Another technique for drug screening which may be used provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with HTES, or fragments thereof, and washed. Bound HTES is then detected by methods well known in the art. Purified HTES can also be coated directly onto plates for use in the aforementioned drug screening techniques. Alternatively, non-neutralizing antibodies can be used to capture the peptide and immobilize it on a substrate.

In another embodiment, one may use competitive drug screening assays in which neutralizing antibodies capable of binding HTES specifically compete with a test compound for binding HTES. In this manner, antibodies can be used to detect the presence of any peptide which shares one or more antigenic determinants with HTES.

In additional embodiments, the nucleotide sequences which encode HTES may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. NEUTFMT01 cDNA Library Construction

The peripheral blood granulocyte cDNA library was constructed using cells isolated from buffy coat units obtained from unrelated male and female donors. Peripheral blood granulocytes were collected by density gradient centrifugation through Ficoll-Hypaque. Cells were cultured in 10 nM fMLP for 30 minutes, lysed in GuSCN, and spun through CsCl to obtain RNA for library construction. cDNA synthesis was initiated using an XhoI-oligo d(T) primer. Double-stranded cDNA was blunted, ligated to EcoRI adaptors, digested with XhoI, size-selected, and cloned into the XhoI and EcoRI sites of the λ UNIZAP plasmid (Stratagene).

II. Isolation and Sequencing of cDNA Clones

Plasmid DNA was released from the cells and purified using the REAL PREP 96 plasmid kit (QIAGEN, Chatsworth Calif.). The recommended protocol was employed except for the following changes: 1) the bacteria were cultured in 1 ml of sterile Terrific Broth (Life Technologies) with carbenicillin (carb) at 25 mg/l and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were prepared using a MICROLAB 2200 system (Hamilton) in combination with DNA ENGINE thermal cyclers (MJ Research) and sequenced by the method of Sanger and Coulson (1975, J. Mol. Biol. 94: 441f) using ABI PRISM 377 DNA Sequencing systems (PE Biosystems).

III. Homology Searching of cDNA Clones and their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST, Basic Local Alignment Search Tool (Altschul (1993) J. Mol. Evol 36:290–300; Altschul et al. (1990) J. Mol. Biol. 215:403–410).

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith et al. (1992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-10}$ for peptides.

Incyte nucleotide sequences were searched against the GenBank databases for primate (pri), rodent (rod), and other mammalian sequences (mam), and deduced amino acid sequences from the same clones were then searched against GenBank functional protein databases, mammalian (mamp), vertebrate (vrtp), and eukaryote (eukp), for homology.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, supra, ch. 4 and 16.)

Analogous computer techniques applying BLAST are used to search for identical or related molecules in nucleotide databases such as GenBank or the LIFESEQ database (Incyte Pharmaceuticals, Palo Alto Calif.). This analysis is much faster than multiple membrane-based hybridizations. In addition, the sensitivity of the computer search can be modified to determine whether any particular match is categorized as exact or homologous.

The basis of the search is the product score, which is defined as:

$$\frac{\%\text{ sequence identity} \times \%\text{ maximum BLAST score}}{100}$$

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding HTES occurs. Abundance and percent abundance are also reported. Abundance directly reflects the number of times a particular transcript is represented in a cDNA library, and percent abundance is abundance divided by the total number of sequences examined in the cDNA library.

V. Extension of HTES Encoding Polynucleotides

The nucleic acid sequence of Incyte Clone 338680 was used to design oligonucleotide primers for extending a partial nucleotide sequence to full length. One primer was synthesized to initiate extension of an antisense polynucleotide, and the other was synthesized to initiate extension of a sense polynucleotide. Primers were used to facilitate the extension of the known sequence "outward" generating amplicons containing new unknown nucleotide sequence for the region of interest. The initial primers were designed from the cDNA using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (Life Technologies) were used to extend the sequence. If more than one extension is necessary or desired, additional sets of primers are designed to further extend the known region.

High fidelity amplification was obtained by following the instructions for the XL-PCR kit (PE Biosystems) and thoroughly mixing the enzyme and reaction mix. PCR was performed using the DNA ENGINE thermal cycler (MJ Research), beginning with 40 pmol of each primer and the recommended concentrations of all other components of the kit, with the following parameters: Step 1, 94° C. for 1 min (initial denaturation); Step 2, 65° C. for 1 min; Step 3, 68° C. for 6 min; Step 4, 94° C. for 15 sec; Step 5, 65° C. for 1 min; Step 6, 68° C. for 7 min; Step 7, repeat steps 4 through 6 for an additional 15 cycles; Step 8, 94° C. for 15 sec; Step 9, 65° C. for 1 min; Step 10, 68° C. for 7:15 min; Step 11, repeat steps 8 through 10 for an additional 12 cycles; Step 12, 72° C. for 8 min; Step 13, hold at 4° C.

A 5 µl to 10 µl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK kit (QIAGEN), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2 to 3 hours, or overnight at 16° C. Competent E. coli cells (in 40 µl of appropriate media) were transformed with 3 µl of ligation mixture and cultured in 80 µl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing 2× carb. The following day, several colonies were randomly picked from each plate and cultured in 150 µl of liquid LB/2× carb medium placed in an individual well of an appropriate commercially-available sterile 96-well microtiter plate. The following day, 5 µl of each overnight culture was transferred into a non-sterile 96-well plate and, after dilution 1:10 with water, 5 µl from each sample was transferred into a PCR array.

For PCR amplification, 18 µl of concentrated PCR reaction mix (3.3×) containing 4 units of rTth DNA polymerase, a vector primer, and one or both of the gene specific primers used for the extension reaction were added to each well. Amplification was performed using the following conditions: Step 1, 94° C. for 60 sec; Step 2, 94° C. for 20 sec; Step 3, 55° C. for 30 sec; Step 4, 72° C. for 90 sec; Step 5, repeat steps 2 through 4 for an additional 29 cycles; Step 6, 72° C. for 180 sec; Step 7, hold at 4° C.

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 is used to obtain 5' regulatory sequences using the procedure above, oligonucleotides designed for 5' extension, and an appropriate genomic library.

VI. Labeling and use of Individual Hybridization Probes

Hybridization probes derived from SEQ ID NO:2 employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer and 250 µCi of [$\gamma$-$^{32}$P] adenosine triphosphate (APB) and T4 polynucleotide kinase (NEN Life Science Products, Boston Mass.). The labeled oligonucleotides are substantially purified using a SEPHADEX G-25 superfine resin column (ABP). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba 1, or Pvu II (NEN Life Science Products).

The DNA from each digest is fractionated on a 0.7 percent agarose gel and transferred to a NYTRANPLUS membrane (Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR film (Eastman Kodak, Rochester N.Y.) is exposed to the blots in a PHOSPHOIMAGER cassette (APB) hybridization patterns are compared.

VII. Microarrays

To produce oligonucleotides for a microarray, one of the nucleotide sequences of the present invention is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies approximately 20 sequence-specific oligonucleotides of 20 nucleotides in length (20-mers). A matched set of oligonucleotides are created in which one nucleotide in the center of each sequence is altered. This process is repeated for each gene in the microarray, and double sets of twenty 20-mers are synthesized and arranged on the surface of the silicon chip using a light-directed chemical process. (See, e.g., Chee, supra.)

In the alternative, a chemical coupling procedure and an ink jet device are used to synthesize oligomers on the surface of a substrate. (See, e.g., Baldeschweiler, supra.) In another alternative, a grid array analogous to a dot or slot blot is used to arrange and link cDNA fragments or oligonucleotides to the surface of a substrate using a vacuum system or thermal, UV, mechanical, or chemical bonding procedures. A typical array may be produced by hand or using available materials and machines and contain grids of 8 dots, 24 dots, 96 dots, 384 dots, 1536 dots, or 6144 dots. After hybridization, the microarray is washed to remove nonhybridized probes, and a scanner is used to determine the levels and patterns of fluorescence. The scanned image is examined to determine the degree of complementarity and the relative abundance/ expression level of each oligonucleotide sequence in the microarray.

VIII. Complementary Polynucleotides

Sequences complementary to the HTES-encoding sequences, or any parts thereof, are used to detect, decrease, or inhibit expression of naturally occurring HTES. Although use of oligonucleotides comprising from about 15 to 30 base pairs is described, essentially the same procedure is used with smaller or with larger sequence fragments. Appropriate oligonucleotides are designed using Oligo 4.06 software and the coding sequence of HTES. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HTES-encoding transcript.

IX. Expression of HTES

Expression of HTES is accomplished by subcloning the cDNAs into appropriate vectors and transforming the vectors into host cells. In this case, the cloning vector is also used to express HTES in E. coli. This vector contains a promoter for β-galactosidase upstream of the cloning site, followed by sequence containing the amino-terminal Met and the subsequent seven residues of β-galactosidase. Immediately following these eight residues is a bacteriophage promoter useful for transcription and a linker containing a number of unique restriction sites.

Induction of an isolated, transformed bacterial strain with isopropyl beta-D-thiogalactopyranoside using standard methods produces a fusion protein which consists of the first 8 residues of β-galactosidase, about 5 to 15 residues of linker, and the full length protein. The signal residues direct the secretion of HTES into bacterial growth media which can be used directly in the following assay for activity.

X. Demonstration of HTES Activity

The activity of HTES is determined by it's ability to promote differentiation of permeabilized C2 muscle cells. The basis of this assay lies in the ability of LIM-only proteins to substitute for muscle LIM protein (MLP) in promoting the differentiation of mouse C2 myogenic cells. Shifting C2 cells from high serum medium to low-serum medium induces differentiation of these cells, wherein they change from round cells to spindle-shaped cells. In addition, the cells express myotubules and other cytoskeletal components characteristic of a mature muscle cell. C2 cells which have been stably transformed with a vector expressing antisense to the MLP message (C2-AS cells) do not undergo differentiation following a shift to low-serum media. However, these cells can be induced to undergo differentiation under these conditions provided they are permeabilized and exposed to purified MLP or transiently transfected with a vector expressing MLP. In addition, other LIM-only proteins including Drosophila homolog of MLP (DMLP) and CRIP, are able to substitute for MLP in promoting differentiation of C2-AS cells. Thus, the activity of a sample containing HTES is assayed by determining it's ability to promote differentiation in C2-AS cells. Following permeabilization and treatment with HTES-containing samples, the degree of differentiation of C2-AS cells is measured by visual examination, e.g., scoring the cells for the change in morphology characteristic of differentiated C2-AS cells as described in Arber et al (1994; Cell 79:221–231).

XI. Production of HTES Specific Antibodies

HTES substantially purified using PAGE electrophoresis (see, e.g., Harrington (1990) Methods Enzymol. 182:488495), or other purification techniques, is used to immunize rabbits and to produce antibodies using standard protocols. The HTES amino acid sequence is analyzed using LASERGENE software (DNASTAR) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel, supra, ch. 11.)

Typically, the oligopeptides are 15 residues in length, and are synthesized using an ABI 43 1A peptide synthesizer using Fmoc-chemistry and coupled to KLH (Sigma-Aldrich, St. Louis Mo.) by reaction with N-maleimidobenzoyl-N-hydroxysuccinimide ester. (See, e.g., Ausubel, supra.) Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XII. Purification of Naturally Occurring HTES using Specific Antibodies

Naturally occurring or recombinant HTES is substantially purified by immunoaffinity chromatography using antibodies specific for HTES. An immunoaffinity column is constructed by covalently coupling HTES antibody to an activated chromatographic resin, such as CNBr-activated SEPHAROSE beads (APB). After the coupling, the resin is blocked and washed according to the manufacturer's instructions.

Media containing HTES are passed over the immunoaffinity column, and the column is washed under conditions that allow the preferential absorbance of HTES (e.g., high ionic strength buffers in the presence of detergent). The column is eluted under conditions that disrupt antibody/HTES binding (e.g., a buffer of pH 2 to pH 3, or a high concentration of a chaotrope, such as urea or thiocyanate ion), and HTES is collected.

XIII. Identification of Molecules which Interact with HTES

HTES or biologically active fragments thereof are labeled with $^{125}$I Bolton-Hunter reagent (Bolton et al. (1973) Biochem. J. 133:529–539). Candidate molecules previously arrayed in the wells of a multi-well plate are incubated with the labeled HTES, washed, and any wells with labeled HTES complex are assayed. Data obtained using different concentrations of HTES are used to calculate values for the number, affinity, and association of HTES with the candidate molecules.

All patents and publications are incorporated by reference herein. Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A method of preparing a polyclonal antibody comprising:
   (a) immunizing an animal with the polypeptide having the amino acid sequence of SEQ ID NO:1 under conditions to elicit an antibody response;
   (b) isolating animal antibodies; and
   (c) screening the isolated antibodies with the polypeptide thereby identifying a polyclonal antibody which binds specifically to the polypeptide having the amino acid sequence of SEQ ID NO:1.

2. A method of making a monoclonal antibody comprising:
   a) immunizing an animal with the polypeptide having the amino acid sequence of SEQ ID NO:1 under conditions to elicit an antibody response;
   b) isolating antibody-producing cells from the animal;
   c) fusing the antibody-producing cells with immortalized cells in culture to form monoclonal antibody-producing hybridoma cells;
   d) culturing the hybridoma cells; and
   e) isolating from the culture monoclonal antibodies which bind specifically to the polypeptide having the amino acid sequence of SEQ ID NO:1.

* * * * *

SEQUENCE LISTING (1) GENERAL INFORMATION:

(iii) NUMBER OF SEQUENCES: 3

(2) INFORMATION FOR SEQ ID NO:1:

(i) SEQUENCE CHARACTERISTICS:
      (A) LENGTH: 421 amino acids
      (B) TYPE: amino acid
      (C) STRANDEDNESS: single
      (D) TOPOLOGY: linear (vii) IMMEDIATE SOURCE:

(A) LIBRARY: NEUTFMT01
        (B) CLONE: 33860

(xi) SEQUENCE DESCRIPTION: SEQ ID NO:1:

Met Asp Leu Glu Asn Lys Val Lys Lys Met Gly Leu Gly His Glu Gln
1               5                   10                  15

Gly Phe Gly Ala Pro Cys Leu Lys Cys Lys Glu Lys Cys Glu Gly Phe
            20                  25                  30

Glu Leu His Phe Trp Arg Lys Ile Cys Arg Asn Cys Lys Cys Gly Gln
        35                  40                  45

Glu Glu His Asp Val Leu Leu Ser Asn Glu Glu Asp Arg Lys Val Gly
    50                  55                  60

Lys Leu Phe Glu Asp Thr Lys Tyr Thr Thr Leu Ile Ala Lys Leu Lys
65                  70                  75                  80

Ser Asp Gly Ile Pro Met Tyr Lys Arg Asn Val Met Ile Leu Thr Asn
                85                  90                  95

Pro Val Ala Ala Lys Lys Asn Val Ser Ile Asn Thr Val Thr Tyr Glu
            100                 105                 110

Trp Ala Pro Pro Val Gln Asn Gln Ala Leu Ala Arg Gln Tyr Met Gln
        115                 120                 125

Met Leu Pro Lys Glu Lys Gln Pro Val Ala Gly Ser Glu Gly Ala Gln
130                 135                 140

Tyr Arg Lys Lys Gln Leu Ala Lys Gln Leu Pro Ala His Asp Gln Asp
145                 150                 155                 160

Pro Ser Lys Cys His Glu Leu Ser Pro Arg Glu Val Lys Glu Met Glu
                165                 170                 175

Gln Phe Val Lys Lys Tyr Lys Ser Glu Ala Leu Gly Val Gly Asp Val
            180                 185                 190

Lys Leu Pro Cys Glu Met Asp Ala Gln Gly Pro Lys Gln Met Asn Ile
        195                 200                 205

Pro Gly Gly Asp Arg Ser Thr Pro Ala Ala Val Gly Ala Met Glu Asp
210                 215                 220

Lys Ser Ala Glu His Lys Arg Thr Gln Tyr Ser Cys Tyr Cys Cys Lys
225                 230                 235                 240

Leu Ser Met Glu Glu Gly Asp Pro Ala Ile Tyr Ala Glu Arg Ala Gly
                245                 250                 255

Tyr Asp Lys Leu Trp His Pro Ala Cys Phe Val Cys Ser Thr Cys His
            260                 265                 270

Glu Leu Leu Val Asp Met Ile Tyr Phe Trp Lys Asn Glu Lys Leu Tyr
        275                 280                 285

Cys Gly Arg His Tyr Cys Asp Ser Glu Lys Pro Arg Cys Ala Gly Cys
    290                 295                 300

Asp Glu Leu Ile Phe Ser Asn Glu Tyr Thr Gln Ala Glu Asn Gln Asn
305                 310                 315                 320

Trp His Leu Lys His Phe Cys Cys Phe Asp Cys Asp Ser Ile Leu Ala
                325                 330                 335

Gly Glu Ile Tyr Val Met Val Asn Asp Lys Pro Val Cys Lys Pro Cys
            340                 345                 350

Tyr Val Lys Asn His Ala Val Val Cys Gln Gly His Asn Ala Ile
        355                 360                 365

Asp Pro Glu Val Gln Arg Val Thr Tyr Asn Asn Phe Ser Trp His Ala
    370                 375                 380

Ser Thr Glu Cys Phe Leu Cys Ser Cys Ser Lys Cys Leu Ile Gly
385                 390                 395                 400

```
Gln Lys Phe Met Pro Val Glu Gly Met Val Phe Cys Ser Val Glu Cys
            405                 410                 415
Lys Lys Arg Met Ser
        420

(2) INFORMATION FOR SEQ ID NO:2:

(i) SEQUENCE CHARACTERISTICS:
        (A) LENGTH: 2097 base pairs
        (B) TYPE: nucleic acid
        (C) STRANDEDNESS: single
        (D) TOPOLOGY: linear (vii) IMMEDIATE SOURCE:
        (A) LIBRARY: NEUTFMT01
        (B) CLONE: 338680

(xi) SEQUENCE DESCRIPTION: SEQ ID NO:2:

GGAAGTTCGA CGGCGCCGGG CGAGTGGCTG TTGAGCGGCG CCGCGGGAGT TCCGCAGGTT    60

TCCCGTGTTC GCAGCGGAGC CGGAGGCAGC TGAACCCGGC CGTGGGATCC CGGATAGGAG   120

GAGGAGGGGA CCCATAGGAC GCGTTAACAT GGACCTGGAA AACAAAGTGA AGAAGATGGG   180

CTTAGGTCAC GAGCAAGGAT TTGGAGCCCC TTGTTTAAAA TGCAAAGAAA ATGTGAAGG    240

ATTCGAACTG CACTTCTGGA GAAAAATATG TCGTAACTGC AAGTGTGGCC AAGAAGAGCA   300

TGATGTCCTC TTGAGCAATG AAGAGGATCG AAAAGTGGGA AAACTTTTTG AAGACACCAA   360

GTATACCACT CTGATTGCAA AACTAAAGTC AGATGGAATT CCATGTATA AACGCAATGT   420

TATGATATTG ACGAATCCAG TTGCTGCCAA GAAGAATGTC TCCATCAATA CAGTTACCTA   480

TGAGTGGGCT CCTCCTGTCC AGAATCAAGC ATTGGCCAGG CAGTACATGC AGATGCTACC   540

CAAGGAAAAG CAGCCAGTAG CAGGCTCAGA GGGGGCACAG TACCGGAAGA AGCAGCTGGC   600

AAAGCAGCTC CCTGCACATG ACCAGGACCC TTCAAAGTGC CATGAGTTGT CTCCCAGAGA   660

GGTGAAGGAG ATGGAGCAGT TTGTGAAGAA ATATAAGAGC GAAGCTCTGG GAGTAGGAGA   720

TGTCAAACTT CCCTGTGAGA TGGATGCCCA AGGCCCCAAA CAAATGAACA TTCCTGGAGG   780

GGATAGAAGC ACCCCAGCAG CAGTGGGGGC CATGGAGGAC AAATCTGCTG AGCACAAAAG   840

AACTCAATAT TCCTGCTATT GCTGCAAACT GAGTATGGAA GAAGGTGACC CAGCCATCTA   900

TGCCGAAAGG GCTGGCTATG ATAAACTGTG GCACCCAGCT TGTTTTGTCT GCAGCACCTG   960

CCATGAACTC CTGGTTGACA TGATTTATTT TTGGAAGAAT GAGAAGCTAT ACTGTGGCAG  1020

ACATTACTGT GACAGCGAGA AACCCCGATG TGCTGGCTGT GACGAGCTGA TATTCAGCAA  1080

TGAGTATACC CAGGCAGAAA ACCAGAATTG GCACCTGAAA CACTTCTGCT GCTTTGACTG  1140

TGATAGCATT CTAGCTGGGG AGATATACGT GATGGTCAAT GACAAGCCCG TGTGCAAGCC  1200

CTGCTATGTG AAGAATCACG CTGTGGTGTG TCAAGGATGC CACAATGCCA TCGACCCAGA  1260

AGTGCAGCGG GTGACCTATA ACAATTTCAG CTGGCATGCA TCCACAGAGT GCTTTCTGTG  1320

CTCTTGCTGC AGCAAATGCC TCATTGGGCA GAAGTTCATG CCAGTAGAAG GGATGGTTTT  1380

CTGTTCAGTG GAATGTAAGA AGAGGATGTC TTAGGAGGAG GGCACCCAGA AGTATCGAGC  1440

CATAGCTATC CAAAGTGGTC TGCATTTCTA CTGTAAAATG CAATTTGAAA AAAATAAAAC  1500

GCAAAAAAG AAACTGTAAA GGAAACCAAG AGATTTGTT TAATTTTTTT GGCCATTTTT    1560

TCTTCATCAA TTTTTTTTCG GTCTCAACTT TTAAACTTGG TTTAAGCATT TGATTTGTAA  1620

AACAGTAAAT AATTGTATCT TTCCATAGCT TTTCAAATGT GAAATCATTT TTGGAAGCTT  1680

GGATCTCATT AAACTTCATG TCTCTATTCC ATTTGTGCCA CACACTTAAA AGTTAGTGTA  1740
```

-continued

```
CTGAATGGAA AGATGAGCAT TCCTAGTTCT ACACTTCTTT TTTCCCCCTC ATGTGTAAAA      1800

TGAAAAGAAA ACTAAATTTG CCCTAATACC AAGGCGCTAC GTTTATTGCC TCGTCTTATT      1860

CCATGACCTT TGTAATGATA CACAGTGAAT TCTTTTTGAC AAAGAGAAAT GCCGTGTAGT      1920

ATGCCGAGCT GCTGTTTTAA TGCCTATGCA TTTACTCTTT TCTGATTTAG GCAAAAGTGG      1980

CATTTCCTTA ATGCATTTCT CAATTTTTTA AAGGACCCTA CTTCAGAATC CCCTTTGAAG      2040

TTGTGACTTG AACGGTGGCC TGAAATTTTA TTACCCCTGG GGCATAACAG ATCCCCC        2097
```

(2) INFORMATION FOR SEQ ID NO:3:

(i) SEQUENCE CHARACTERISTICS:
        (A) LENGTH: 421 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 475210

(xi) SEQUENCE DESCRIPTION: SEQ ID NO:3:

```
Met Asp Leu Glu Asn Lys Val Lys Lys Met Gly Leu Gly His Glu Gln
 1               5                  10                  15

Gly Phe Gly Ala Pro Cys Leu Lys Cys Lys Glu Lys Cys Glu Gly Phe
            20                  25                  30

Glu Leu His Phe Trp Arg Lys Ile Cys Arg Asn Cys Lys Cys Gly Gln
        35                  40                  45

Glu Glu His Asp Val Leu Leu Ser Asn Glu Glu Asp Arg Lys Val Gly
    50                  55                  60

Lys Leu Phe Glu Asp Thr Lys Tyr Thr Thr Leu Ile Ala Lys Leu Lys
65                  70                  75                  80

Ser Asp Gly Ile Pro Met Tyr Lys Arg Asn Val Met Ile Leu Thr Asn
                85                  90                  95

Pro Val Ala Ala Lys Lys Asn Val Ser Ile Asn Thr Val Thr Tyr Glu
           100                 105                 110

Trp Ala Pro Pro Val Gln Asn Gln Ala Leu Ala Arg Gln Tyr Met Gln
       115                 120                 125

Met Leu Pro Lys Glu Lys Gln Pro Val Ala Gly Ser Glu Gly Ala Gln
   130                 135                 140

Tyr Arg Lys Lys Gln Leu Ala Lys Gln Leu Pro Ala His Asp Gln Asp
145                 150                 155                 160

Pro Ser Lys Cys His Glu Leu Ser Pro Arg Glu Val Lys Glu Met Glu
                165                 170                 175

Gln Phe Val Lys Lys Tyr Lys Ser Glu Ala Leu Gly Val Gly Asp Val
           180                 185                 190

Lys Leu Pro Cys Glu Met Asp Ala Gln Gly Pro Lys Gln Met Asn Ile
       195                 200                 205

Pro Gly Gly Asp Arg Ser Thr Pro Ala Ala Val Gly Ala Met Glu Asp
   210                 215                 220

Lys Ser Ala Glu His Lys Arg Thr Gln Tyr Ser Cys Tyr Cys Cys Lys
225                 230                 235                 240

Leu Ser Met Glu Glu Gly Asp Pro Ala Ile Tyr Ala Glu Arg Ala Gly
                245                 250                 255

Tyr Asp Lys Leu Trp His Pro Ala Cys Phe Val Cys Ser Thr Cys His
           260                 265                 270
```

```
Glu Leu Leu Val Asp Met Ile Tyr Phe Trp Lys Asn Glu Lys Leu Tyr
        275                 280                 285

Cys Gly Arg His Tyr Cys Asp Ser Glu Lys Pro Arg Cys Ala Gly Cys
        290                 295                 300

Asp Glu Leu Ile Phe Ser Asn Glu Tyr Thr Gln Ala Glu Asn Gln Asn
305                     310                 315                 320

Trp His Leu Lys His Phe Cys Cys Phe Asp Cys Asp Ser Ile Leu Ala
                325                 330                 335

Gly Glu Ile Tyr Val Met Val Asn Asp Lys Pro Val Cys Lys Pro Cys
                340                 345                 350

Tyr Val Lys Asn His Ala Val Val Cys Gln Gly Cys His Asn Ala Ile
        355                 360                 365

Asp Pro Glu Val Gln Arg Val Thr Tyr Asn Asn Phe Ser Trp His Ala
        370                 375                 380

Ser Thr Glu Cys Phe Leu Cys Ser Cys Ser Lys Cys Leu Ile Gly
385                     390                 395                 400

Gln Lys Phe Met Pro Val Glu Gly Met Val Phe Cys Ser Val Glu Cys
                405                 410                 415

Lys Lys Arg Met Ser
                420

(2) INFORMATION FOR SEQ ID NO:4:

(i) SEQUENCE CHARACTERISTICS:
        (A) LENGTH: 51 amino acids
        (B) TYPE: amino acid
        (C) STRANDEDNESS: single
        (D) TOPOLOGY: linear (xi) SEQUENCE DESCRIPTION: SEQ ID NO:4:

Cys Xaa Cys Xaa Xaa Xaa Xaa Xaa Xaa Xaa Xaa Xaa Xaa Xaa Xaa Xaa Xaa
1               5                   10                  15

Xaa His Xaa Xaa Cys Xaa Xaa Cys Xaa Xaa Cys Xaa Xaa Xaa Xaa Xaa Xaa
20                  25                  30                  35

Xaa Xaa Xaa Xaa Xaa Xaa Xaa Xaa Cys Xaa Xaa Cys
        40                  45                  50
```